(12) United States Patent
Veraart et al.

(10) Patent No.: US 6,442,431 B1
(45) Date of Patent: Aug. 27, 2002

(54) DEVICE AND METHOD FOR PRODUCTION OF VISUAL SENSATIONS BY OPTIC NERVE STIMULATION

(75) Inventors: Claude G. Veraart, Brussels (BE); J. Thomas Mortimer, Chagrin Falls, OH (US)

(73) Assignee: Axon Engineering, Inc.,, Garfield Heights, OH (US)

( * ) Notice: Subject to any disclaimer, the term of this patent is extended or adjusted under 35 U.S.C. 154(b) by 0 days.

(21) Appl. No.: 09/622,464

(22) PCT Filed: Jul. 23, 1999

(86) PCT No.: PCT/US99/16793
§ 371 (c)(1),
(2), (4) Date: Aug. 17, 2000

(87) PCT Pub. No.: WO00/06248
PCT Pub. Date: Feb. 10, 2000

Related U.S. Application Data
(60) Provisional application No. 60/094,266, filed on Jul. 27, 1998, and provisional application No. 60/100,492, filed on Sep. 16, 1998.

(51) Int. Cl.$^7$ ............................. A61N 1/32; A61N 1/00
(52) U.S. Cl. ............................................................ 607/54
(58) Field of Search ........................................... 607/54

(56) References Cited

U.S. PATENT DOCUMENTS 4,979,508 A * 12/1990 Beck ............................ 607/54
5,674,263 A * 10/1997 Yamamoto et al. ........... 607/54

FOREIGN PATENT DOCUMENTS

DE        197 50 043 A1 * 11/1997      ............. A61N/1/05
JP         63-296772       * 12/1988      ............. A61N/1/32

* cited by examiner

Primary Examiner—Carl Layno
(74) Attorney, Agent, or Firm—Jerrold J. Litzinger

(57) ABSTRACT

A method and device for producing visual sensations within blind persons includes installing a self-sizing spiral nerve cuff electrode about the optic nerve of a blind person then transmitting electrical pulses to the nerve to generate phosphenes within the patient's visual field.

14 Claims, 4 Drawing Sheets

DEVICE AND METHOD FOR PRODUCTION OF VISUAL SENSATIONS BY OPTIC NERVE STIMULATION

CROSS-REFERENCE TO RELATED APPLICATIONS

This is a utility patent application claiming priority from provisional U.S. Patent Application Ser. No. 60/094,266 filed Jul. 27, 1998, and also from provisional U.S. Patent Application Ser. No. 60/100,492, filed Sep. 16, 1998.

BACKGROUND OF THE INVENTION

Field of the Invention

The present invention relates generally to a method and device for inducing visual sensations within persons suffering from blindness, and, in particular to a method and device for restoring some visual function within the eyes of blind persons by encircling the optic nerve with a self sizing cuff electrode which is electrically stimulated.

Blindness is an affliction which affects more that 42 million persons worldwide. Many causes of blindness, especially those involving occlusions or opacity in the optical pathway through the eye, have yielded to medical treatments and vision can now be restored to a great extent in a large number of cases. Some diseases of the eye, however, cause blindness by attacking the light sensing retina, causing blindness while the remainder of the optical pathway remains functional. A variety of retinal diseases, for example, cause vision loss or blindness by destruction of the choroid, choriocapallaris, and the outer retinal layers. In several retinal degenerative diseases, select populations of photoreceptor cells are lost. Specifically, in macular degeneration and retinitis pigmentosa, the retinal photoreceptors degenerate while other cells in the retina as well as the retina's central connections are maintained; the complex synaptic interconnections at the outer plexiform layer of the eye that would normally transmit photosignals to the nerve ganglions are intact, as are the ganglion axons or bundles which make up the optic nerve, which normally transmits the visual information to the brain.

Numerous efforts have been made over the years to develop devices which could help to remedy retinal blindness. In the 1930's, Forester investigated the effect of electrically stimulating the exposed occipital pole of one cerebral hemisphere. He found that when a point at the extreme occipital pole was stimulated, the patient perceived a small spot of light directly in front and motionless, which spots are known as phosphenes. Subsequently, in the 1960's Brindley and Lewin thoroughly studied electrical stimulation of the human occipital cortex. By varying the stimulation parameters, the investigators described in detail the locations of the phosphenes produced relative to the specific region of the occipital cortex stimulated. These experiments demonstrated: the consistent shape and position of phosphenes; that increased stimulation pulse duration made phosphenes brighter; and that there was no detectable interaction between neighboring electrodes which were as close as 2.4 mm apart.

In recent years, several alternative procedures have been proposed for the restoration of vision. One procedure involves the implantation of a tissue graft or cells into the host retina. One example of this procedure is taught in U.S. Pat. No. 5,817,075.

Another procedure which as been attempted uses electrodes or electrical fields in combination with photosensitive devices to stimulate neurons or ganglion cells. For example, U.S. Pat. No. 4,628,933 is directed to a visual prosthesis having a close packed array of photosensitive devices which are coupled to a plurality of electrodes that stimulate neurons at the surface of the retina in a pattern corresponding to the illumination pattern of the photosensitive array. U.S. Pat. No. 5,109,844 describes a retinal microstimulator for stimulating retinal ganglion cells by the use of a plurality of electrodes for recognition. U.S. Pat. No. 5,147,284 teaches an electromagnetic field radiator and receiver which produce an effect of electrostimulation of the optic nerve and retina by a pulsed magnetic field. Finally, U.S. Pat. No. 5,873,901 uses a thin film optical detector based on a dielectric capacitor that can be implanted onto the retina which can produce a signal at the brain down from the optic nerve that may be perceived as light.

A great variety of electrodes have been developed for application of electrical stimulation. Electrodes intended to stimulate motor nerve fibers include electrodes placed on the surface of the skin, percutaneous intramuscular electrodes, surgically implanted intramuscular electrodes, and epimysial electrodes, while electrodes placed directly on or in peripheral nerve trunks include epineural electrodes, penetrating epineural electrodes, wire and silicon intraneural electrodes.

A different hurdle in the development of a visual prosthesis has been the development of an electrode suitable for chronic implant which can provide stimuli to the optic nerve. The present invention overcomes these and other problems by the use of a self-sizing spiral cuff electrode around the optic nerve.

SUMMARY OF THE INVENTION

It is therefore an object of the present invention to provide a method of inducing visual sensation within blind persons by generating electrical stimuli to the optic nerve via a self-sizing spiral cuff electrode.

It is also an object of the present invention to provide a device which can be implanted intracranially within a patient.

It is a further object of the present invention to produce localized visual sensations in blind persons which can be varied by changing the magnitude of the stimulus.

These and other objects of the present invention are accomplished by the use of a signal generating means which transmits a series of pulses to the optic nerve of a blind patient via a self-sizing cuff electrode to activate the nerve, whereby the patient is able to visualize a series of phosphenes with broad distribution within the visual field.

DETAILED DESCRIPTION OF THE PREFERRED EMBODIMENT

Figure 1:
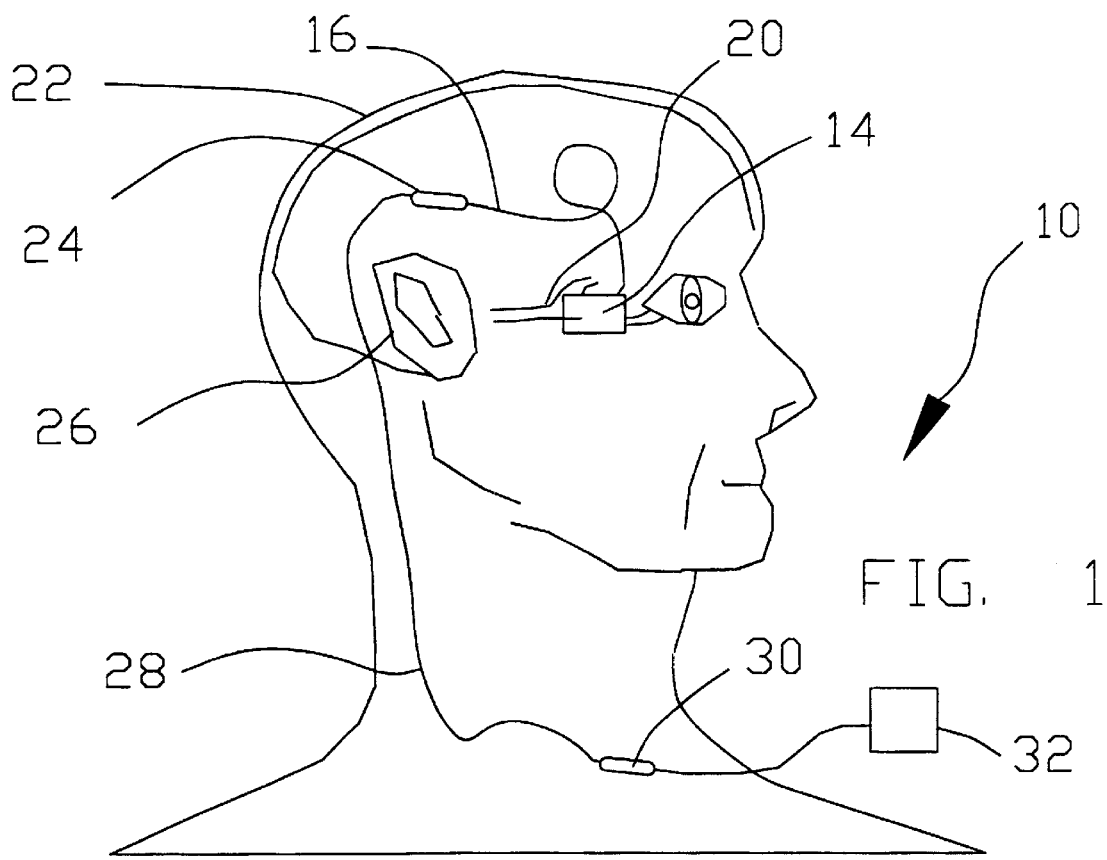
FIG. 1 is a graphic representation of the device of the present invention shown in the installed position in a patient.
Figure 2:
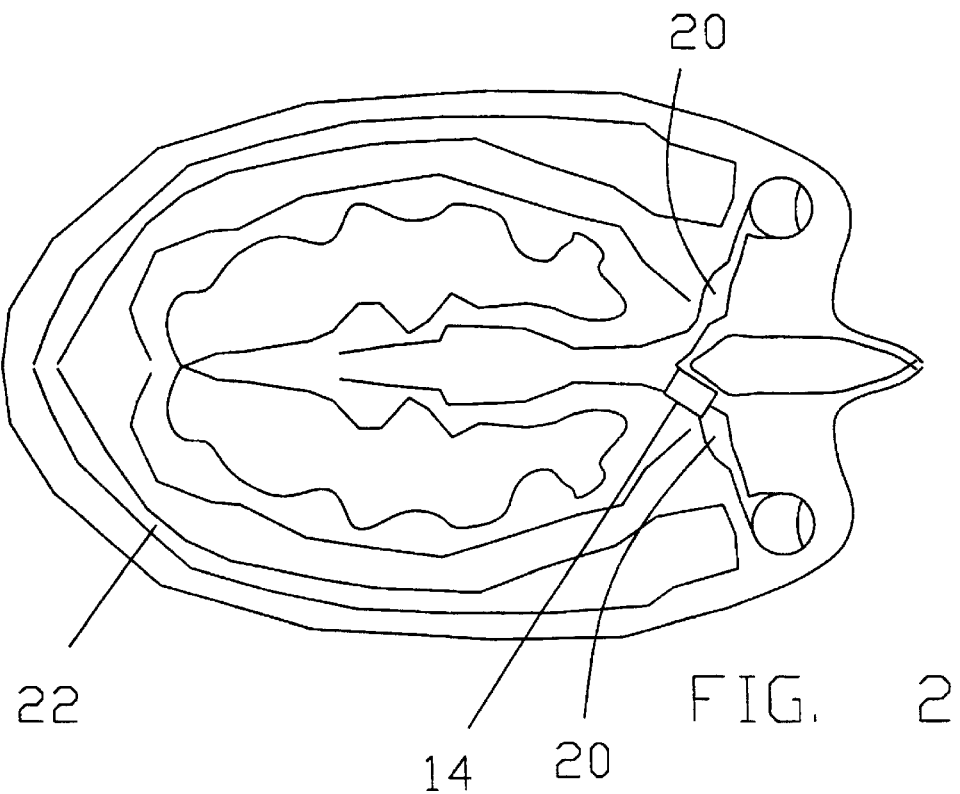
FIG. 2 is a cross-sectional view of the head of the patient showing the position of the device of the present invention.

Referring now to FIGS. 1 and 2, there is shown a prosthetic device, generally indicated at 10, which embodies the principles of the present invention. Device 10 comprises a self-sizing spiral cuff electrode 14 having a lead 16. Electrode 14 is preferably constructed according to the type taught in U.S. Pat. No. 5,505,201 or U.S. Pat. No. 5,324,322, the disclosures of which are incorporated by reference in its entirety for all purposes. The nature of electrode 14 allows it to be positioned about an optic nerve 20 of a patient and permitted to helically curl around and snugly engage the trunk of optic nerve 20, providing intimate and secure electric contact.

To install electrode 14 in position within the skull 22 of the patient, access is gained to skull 22 and electrode 14 is positioned about optic nerve 20 and then released by a unique spiral nerve cuff electrode implantation tool which is described in U.S. patent application Ser. No. 08/986,943. This tool allows electrode 14 to be sequentially released in position about optic nerve 20. Lead 16 from electrode 14 was positioned along the dura mater up to the inferior part of the skull opening. After crossing the dura mater on the lateral aspect of skull 22, lead 16 passes through skull 22 and continues below the skin surface to a subcutaneous connector 24 embedded within skull 22 over the ear 26. A lead 28 from connector 24 passes down the neck and exits the skin below the clavicle terminating with an external connector 30. A controller 32 is coupled to device 10 at connector 30.

The essence of the method and device will now be illustrated by the following case history.

A 59-year old female patient having retinitis pigmentosa was chronically implanted with a device embodying the present invention comprising a self sizing spiral cuff electrode having four contacts installed around the optic nerve. Stimulation started at the hospital on day 2 postsurgery. The patient eventually worked up to a level of two three-hour stimulation sessions a week. Single pulses and pulse trains were both used for stimulation. Stimulation was either monopolar using a surface indifferent anode, or bipolar between two contacts within the electrode cuff. Charge density was always kept below 150 $\mu$C/(cm$^2$ phase) up to 50 Hz [below 50 $\mu$C/(cm$^2$ phase) up to 333 Hz], corresponding to a charge per phase of 300 nC/phase (respectively 100 nC/phase) with a contact area of 0.2 mm$^2$. Determination of current intensity thresholds for generation of a phosphene was always done using the 2 staircase limit method.

To assess phosphene location, a pointing hemisphere, with a radius of 0.45 m was used. The patient's head was maintained in front of the hemispheric surface using a stabilizing frame to support the forehead, chin, and parietal skull, with the right eye positioned at hemisphere center. The right eye EOG was recorded and eye movements were monitored using a TV camera.

When ready for a stimulus, the patient placed her head in a fixed position constrained by the frame, and reached into the hemisphere to place her left index finger on the fixation point, which was a polymer disk at the intersection of the visual axis with the hemisphere. The patient was then instructed to "look at" the fixation point with a steady gaze throughout the stimulation test run. The test run was delimited by two beep sounds, with the left forefinger still in contact with the fixation point, as a proprioceptive reference, the evoked phosphene was then indicated, with the right hand fingers, as a shape on the hemisphere. Phosphene characteristics were recorded, including the following quantities: position dimensions and organization; subjective brightness; dot diameter; foreground and background colors; motion; etc.

After day 118 post surgery, some 1,465 phosphenes had been documented. Transverse thresholds reached generally twice or more the corresponding monopolar thresholds, indirectly confirming proper electrode position. There has been no threshold increase over the time since implantation, and electrical stimuli applied to the contacts in the self-sizing spiral cuff electrode have never evoked sensations other than visual.

Most phosphenes were reported to consist of a set of dots, either in a cluster of 2 to 5, or else arranged in rows, arrays or lumps of 6 to 30. Dot diameter ranged from 8 to 42 minutes of arc (1 to 5.5 mm at the distance of 0.45 m). Occasionally, a kind of surround of lesser brightness was described around each dot in a phosphene. Solid lines, bars, or triangles devoid of dot structure were sometimes reported, usually near perception threshold. Phosphene area (or envelope area for dot phosphenes) generally ranged from 1 to 50 square degrees. Brightness was graded on a scale of 1 to 9 with "very, very weak" graded as 1 and "very, very bright" graded as 9.

Phosphenes were often reported as colored. In the first days postsurgery, they generally appeared to the patient as gold-yellow against a black visual field. Thereafter, blue, white or plain yellow colors were described. with dot phosphenes, the otherwise black visual field sometimes appeared colored in blue, red, or yellow, in between the dots. Occasionally, a solid colored surface (red or yellow) was described adjacent to the envelope of a dot phosphene.

Among the 156 phosphenes collected at the hospital up to day 8 post surgery, 37% were described as moving; most often, they consisted of lines, instead of dots. Afterward, 1,308 of the next 1,309 phosphenes appeared consistently immobile and steady.

Current intensity thresholds were determined using 5 pulse durations (25, 50, 100, 200, and 400 $\mu$s). This study included single pulses, as well as trains of 5, 9, and 17 pulses generated at 40, 80, and 160 Hz respectively. As in the classical strength-duration curve, current intensity thresholds diminished with increasing pulse duration.

Figure 3:
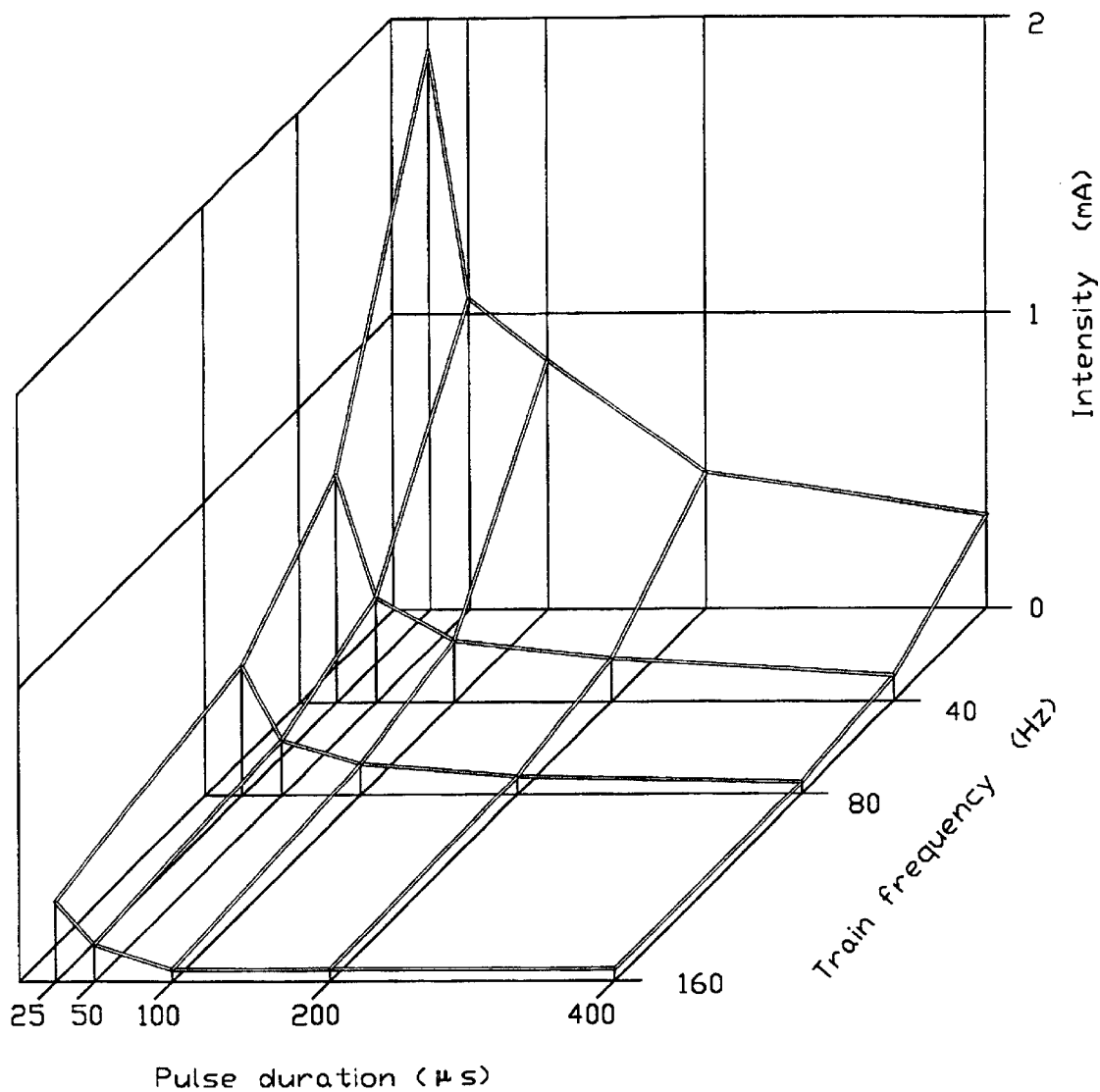
FIG. 3 is a graphic representation showing the current threshold for perception in terms of pulse duration and train frequency.

FIG. 3 depicts a strength-duration frequency surface for this case history. For given values of pulse duration and train frequency, each datum point represents the mean current threshold of the four contacts for perception. By extension, single pulses are referred to as zero frequency. The representation of the classical strength-duration curve, illustrated here in the zero frequency frontal plane, is also shown for trains of 100 ms duration. As a result, a clear drop in perceptual threshold appears along the 5 transverse planes corresponding to the different pulse duration (25, 50, 100, 200, and 400 $\mu$s) when the stimulus frequency increases.

It should be observed that, for a given contact in the cuff electrode, attributes of a phosphene, such as perceived brightness, color, size, organization, position, etc., perceived at threshold for a specific pulse duration and train frequency, usually differed from those documented at threshold for another pulse duration and/or train frequencies. Furthermore, phosphene attributes reported by the patient differed when the same contact was stimulated at different frequencies but at the same values of pulse duration and current.

The attributes of the phosphenes were usually consistent for trials repeated over a short period of time. For example, when, for a first phosphene, standard deviations of center of gravity position as a function of time are 1.1° horizontal and 0.6° vertical (7 measurements made on day 84 for 93 min.), for a second phosphene, they reach 2.6° horizontal and 3.2° vertical (9 measurements made on day 81 for 182 min., and 8 measurements made on day 84 for 101 min.).

Figure 4:
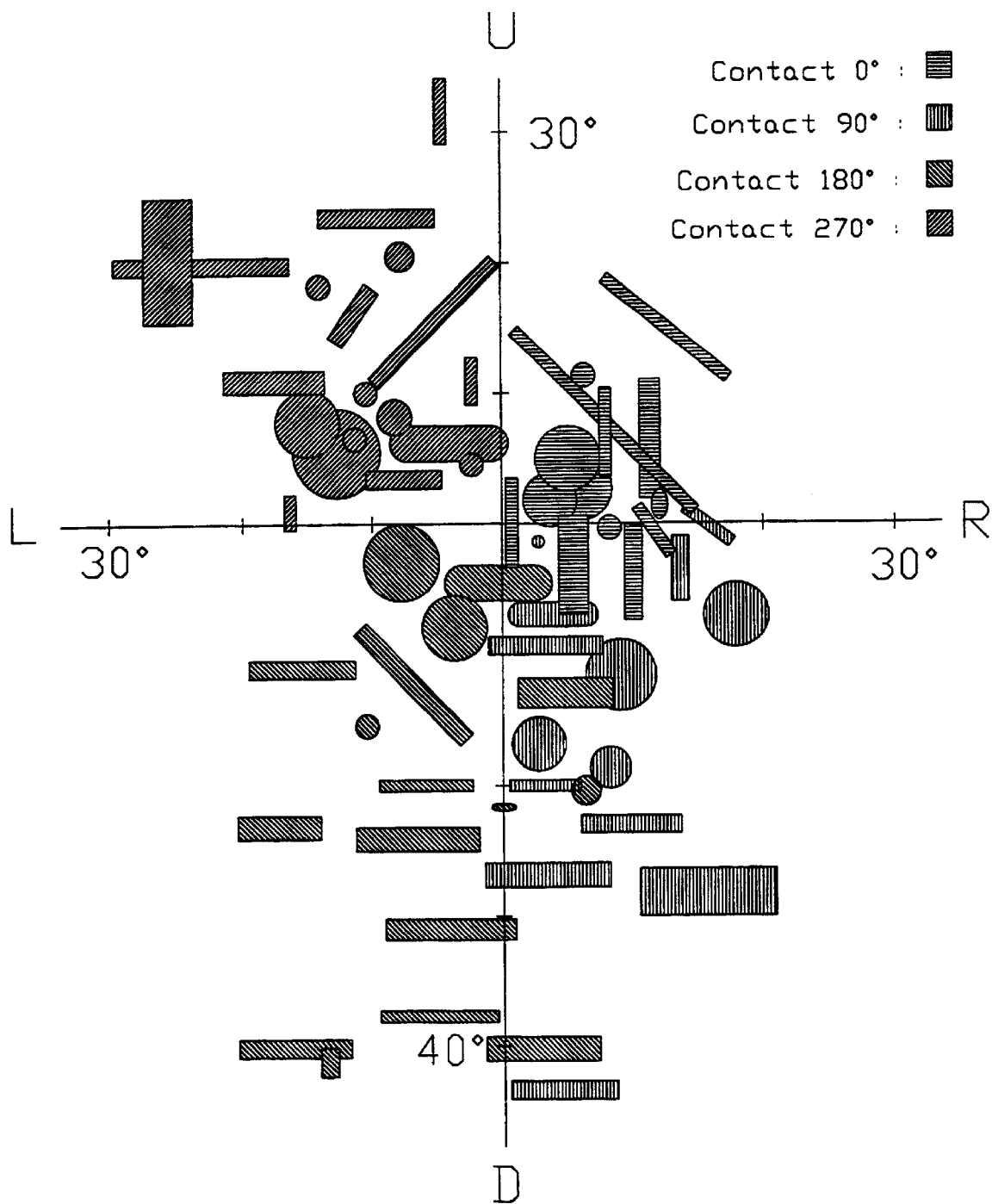
FIG. 4 is a graphic representation of the retinotopic arrangement of phosphenes generated using the present invention.

Localized phosphenes were reported to have been perceived over a larger portion of the visual field, up to 35° upwards and 50° downwards on the vertical meridian and 30° leftwards and 30° rightwards on the horizontal meridian. Near threshold, there appears to be a good retinotopic correspondence between the contact position used for a given stimulation within the cuff electrode and the quadrant of the visual field in which the volunteer drew the related phosphene. FIG. 4 shows a representation of the retinotopic arrangement of phosphenes according to the activated contact in self-sizing spiral cuff electrode 14. When a given stimulating condition was applied to a given contact within the cuff electrode, a phosphene is reported by the patient, provided that the stimulation threshold has been reached. The contact-quadrant relationship which results from the optic nerve electrical activation was consistent with the orderly arrangement of both quadrants and contacts. This sample of 64 phosphenes collected near threshold also illustrates the broad distribution of relatively small phosphenes within the patient's visual field.

Figure 5:
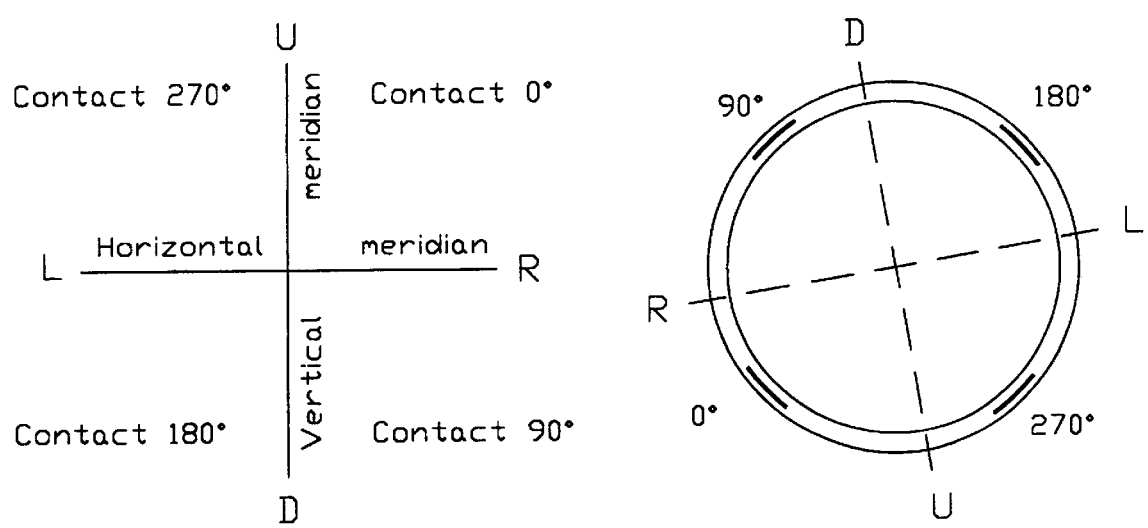
FIG. 5 is a graphic representation of the retinotopic organization of a patient using the present invention.

FIG. 5 shows a representation of the retinotopic organization of the patient's optic nerve. The probable position of the 4 contacts, labeled 0°, 90°, 180°, and 270°, around the optic nerve is indicated on the right, while on the left, the quadrant-contact relationship refers to the position in the visual field of phosphenes elicited when stimulating through a given contact. The retinotopy observed here for the right optic nerve is consistent with previous findings, although with a vertical median slant less slightly than described. When compared to clinical data related to the retinotopy of the human optic nerve, when a slant of about 60° of the vertical meridian optic nerve projection (relative to the vertical axis) is reported, the observed results indicate a more limited inclination.

As expected, phosphene location depend on gaze direction. A steady gaze oriented sideways with respect to the fixation point during the stimulus, or a saccade ending just before the stimulus, resulting in a phosphene location consistently referring to gaze orientation at the time of the electrical stimulation. Similarly, any gaze displacement, either after a time period or immediately after the stimulus, resulted in a phosphene location steadily referring again to gaze orientation at the time of the stimulation (in this case, before the movement). Thus, stimulation resulted in phosphenes coded in spatial coordinates: i.e., the algebraic substraction of gaze coordinates from retinal coordinates frozen at stimulation. Therefore, in order to secure an accurate measurement of phosphene attributes, the importance should be stressed to the patient of maintaining a fixed gaze during the presentation of each test stimulation.

In summary, the axons of retinal ganglion cells in this patient have been successfully activated by electrical stimuli applied to the optic nerve to evoke many distinct phosphenes over a large portion of the visual field. Slight changes in the attributes of the phosphenes seem to occur over time.

While the invention has been shown and described in terms of a preferred embodiment, it will be understood that this invention is not limited to this particular embodiment and that many changes and modifications may be made without departing from the true spirit and scope of the invention as defined in the appended claims.

What is claimed is:

1. A method for stimulating the optic nerve of a mammal to induce visual perception in the eye, comprising the steps of:

implanting a cuff electrode about the optic nerve;

coupling said cuff electrode to a signal generating controller;

and transmitting a series of electrical signals from said controller to the optic nerve through said cuff electrode in order to induce a visual response in the eye.

2. The method of claim 1, wherein said cuff electrode comprises a spiral electrode.

3. The method of claim 2, wherein said electrode is self-sizing.

4. The method of claim 1, wherein said series of electrical signals comprises a bipolar pulse train.

5. The method of claim 1, herein said series of electrical signals comprises pulses having a charge density below 150 $\mu C/(cm^2$ phase).

6. The method of claim 1, wherein said series of electrical signals comprises single pulses.

7. The method of claim 1, whereby said visual response comprises the generation of phosphenes within the visual field of the eye.

8. A device for stimulating the optic nerve of a visually impaired patient, comprising:

a cuff electrode, capable of being positioned about and in contact with the optic nerve of a visually impaired patient;

and control means, electrically coupled to said cuff electrode, for transmitting electrical signals to the optic nerve through said electrode to induce visual perception in said patient.

9. The device of claim 8, wherein said cuff electrode comprises a spiral cuff electrode.

10. The device of claim 9, wherein said electrode is self-sizing.

11. The device of claim 8, wherein said control means generates an electrical pulse train.

12. The device of claim 8, wherein said cuff electrode includes four contacts.

13. The device of claim 8, whereby said electrical signals generate phosphenes within the patient's visual field.

14. The device of claim 8, wherein said electrical signals from said control means stimulate the axons of the retinal ganglion cells of said patient.

* * * * *